US012539228B2

(12) United States Patent
Lyytikäinen et al.

(10) Patent No.: US 12,539,228 B2
(45) Date of Patent: *Feb. 3, 2026

(54) INSERTER

(71) Applicant: Bayer Oy, Turku (FI)

(72) Inventors: Heikki Lyytikäinen, Naantali (FI); Ilkka Jutila, Littoinen (FI); Ulla Calvo Alonso, Piispanristi (FI); Harri Jukarainen, Kuusisto (FI); Taina Träder, Littoinen (FI); Andrew Macleod, Cambridge (GB); Michael Noble, London (GB); David Whitaker, London (GB)

(73) Assignee: Bayer Oy, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 18/524,681

(22) Filed: Nov. 30, 2023

(65) Prior Publication Data

US 2024/0173163 A1 May 30, 2024

Related U.S. Application Data

(63) Continuation of application No. 16/792,748, filed on Feb. 17, 2020, now Pat. No. 11,872,155, which is a
(Continued)

(30) Foreign Application Priority Data

Sep. 17, 2008 (FI) ...................................... 20085870
Sep. 17, 2008 (FI) ...................................... 20085871

(51) Int. Cl.

| | |
|---|---|
| *A61F 6/18* | (2006.01) |
| *A61F 6/14* | (2006.01) |
| *A61M 31/00* | (2006.01) |

(52) U.S. Cl.
CPC ................ *A61F 6/18* (2013.01); *A61F 6/142* (2013.01); *A61M 31/00* (2013.01); *A61F 6/144* (2013.01)

(58) Field of Classification Search
CPC ............ A61F 6/18; A61F 6/142; A61F 6/144; A61M 31/00
See application file for complete search history.

(56) References Cited

U.S. PATENT DOCUMENTS 3,533,406 A 10/1970 Tatum
3,656,483 A 4/1972 Rudel
(Continued)

FOREIGN PATENT DOCUMENTS

CA 1033247 6/1978
CN 1168626 12/1997
(Continued)

OTHER PUBLICATIONS

USPTO Non-Final Office Action mailed in U.S. Appl. No. 13/119,401, Aug. 17, 2012.
(Continued)

*Primary Examiner* — Lauren P Farrar
(74) *Attorney, Agent, or Firm* — IP Spring

(57) ABSTRACT

The present invention relates to an inserter for an intrauterine system comprising a handle (3), and an insertion tube (6) having a first end and a second end, and being arranged in connection with the handle. The inserter is characterized in that the first end of the insertion tube (6) comprises at least one frame slot for receiving a frame of the intrauterine system. The invention also relates to a kit comprising an inserter according to the present invention and an intrauterine system, wherein the intrauterine system (1) comprises a therapeutic component (**1*b*) and a continuous, closed frame (1*a*), the therapeutic component (1*b***) being connected to the
(Continued)

frame (1*a*) at least one point, and therapeutic component (1*b*) of the intrauterine system (1) is at least mainly arranged inside the first end of the insertion tube (6) and the frame (1*a*) of the intrauterine system (1) is at least mainly arranged outside the first end of the insertion tube (6).

18 Claims, 11 Drawing Sheets

Related U.S. Application Data continuation of application No. 15/891,187, filed on Feb. 7, 2018, now Pat. No. 10,561,524, which is a continuation of application No. 15/470,870, filed on Mar. 27, 2017, now abandoned, which is a continuation of application No. 15/245,042, filed on Aug. 23, 2016, now Pat. No. 9,615,965, which is a continuation of application No. 14/088,329, filed on Nov. 22, 2013, now Pat. No. 9,452,082, which is a continuation of application No. 13/771,066, filed on Feb. 19, 2013, now abandoned, which is a continuation of application No. 13/119,401, filed as application No. PCT/FI2009/050738 on Sep. 16, 2009, now abandoned.

(56) References Cited

U.S. PATENT DOCUMENTS

| | | | |
|---|---|---|---|
| 3,783,861 | A | 1/1974 | Abramson |
| 3,794,025 | A | 2/1974 | Lerner |
| 3,896,819 | A | 7/1975 | Zaffaroni et al. |
| 3,902,483 | A | 9/1975 | Place et al. |
| 3,918,444 | A | 11/1975 | Hoff et al. |
| 4,143,656 | A | 3/1979 | Holmes |
| 4,341,728 | A | 7/1982 | Robertson et al. |
| 4,353,363 | A | 10/1982 | Sopena |
| 4,413,985 | A | 11/1983 | Wellner et al. |
| 4,562,835 | A | 1/1986 | Anderson |
| 4,578,075 | A | 3/1986 | Urquhart et al. |
| 4,578,076 | A | 3/1986 | Luukkainen et al. |
| 4,655,204 | A | 4/1987 | Basuyaux |
| 4,678,463 | A | 7/1987 | Millar |
| 4,721,105 | A | 1/1988 | Wildemeersch |
| 4,724,832 | A | 2/1988 | Strubel et al. |
| 4,805,628 | A | 2/1989 | Fry et al. |
| 4,949,732 | A | 8/1990 | Spoon et al. |
| 5,146,931 | A | 9/1992 | Kurz |
| 5,217,450 | A | 6/1993 | Pryor et al. |
| 5,224,493 | A | 7/1993 | Sawan et al. |
| 5,370,129 | A | 12/1994 | Diaz et al. |
| 5,494,047 | A | 2/1996 | Van Os |
| 5,785,053 | A * | 7/1998 | Macandrew .............. A61F 6/18 606/119 |
| 6,056,976 | A | 5/2000 | Markkula et al. |
| 6,103,256 | A | 8/2000 | Nabahi |
| 6,119,696 | A | 9/2000 | Turin |
| 6,278,057 | B1 | 8/2001 | Avellanet |
| 6,299,027 | B1 | 10/2001 | Berge et al. |
| 6,476,079 | B1 | 11/2002 | Jukarainen et al. |
| 6,588,429 | B1 | 7/2003 | Wildemeersch |
| 6,652,548 | B2 | 11/2003 | Evans et al. |
| D525,705 | S | 7/2006 | Luukkainen |
| 7,252,839 | B2 | 8/2007 | Hallinen et al. |
| 7,294,135 | B2 | 11/2007 | Stephens et al. |
| 7,926,488 | B2 | 4/2011 | Luukkainen |
| 8,573,222 | B2 | 11/2013 | Weintraub |
| D718,435 | S | 11/2014 | Deckman et al. |
| 9,452,082 | B2 | 9/2016 | Lyytikainen et al. |
| 9,615,965 | B2 | 4/2017 | Lyytikainen et al. |
| 9,668,912 | B2 | 6/2017 | Jutila et al. |
| D791,318 | S | 7/2017 | Jutila et al. |
| 9,707,123 | B2 | 7/2017 | Lyytikäinen et al. |
| D810,289 | S | 2/2018 | Jutila et al. |
| 10,149,784 | B2 | 12/2018 | Jutila et al. |
| 10,561,524 | B2 | 2/2020 | Lyytikäinen et al. |
| 10,583,035 | B2 | 3/2020 | Lyytikäinen et al. |
| 10,987,244 | B2 | 4/2021 | Jutila et al. |
| 11,432,958 | B2 | 9/2022 | Lyytikäinen et al. |
| 2003/0028236 | A1 | 2/2003 | Gillick et al. |
| 2004/0163650 | A1 * | 8/2004 | Lowe ........................ A61F 6/18 128/830 |
| 2004/0261799 | A1 | 12/2004 | Mock |
| 2005/0178391 | A1 | 8/2005 | Wildemeersch |
| 2005/0274384 | A1 | 12/2005 | Tran et al. |
| 2007/0056591 | A1 | 3/2007 | McSwain |
| 2007/0123904 | A1 | 5/2007 | Stad et al. |
| 2007/0129734 | A1 | 6/2007 | Jutila |
| 2008/0095825 | A1 | 4/2008 | Lafont |
| 2009/0069890 | A1 | 3/2009 | Suri et al. |
| 2009/0105794 | A1 | 4/2009 | Ziarno et al. |
| 2009/0123522 | A1 | 5/2009 | Browning |
| 2010/0049313 | A1 | 2/2010 | Alon et al. |
| 2010/0168563 | A1 | 7/2010 | Braver |
| 2010/0168756 | A1 | 7/2010 | Dorn et al. |
| 2010/0186750 | A1 | 7/2010 | Tran et al. |
| 2010/0280464 | A1 | 11/2010 | De Graaff et al. |
| 2011/0017219 | A1 | 1/2011 | De Graaff et al. |
| 2011/0056501 | A1 | 3/2011 | Kortesuo et al. |
| 2011/0061659 | A1 | 3/2011 | Cruzada et al. |
| 2011/0079226 | A1 | 4/2011 | Sakhel |
| 2011/0146693 | A1 | 6/2011 | Duesterberg et al. |
| 2011/0162656 | A1 | 7/2011 | Jutila et al. |
| 2011/0166508 | A1 | 7/2011 | Lyytikainen et al. |
| 2011/0172593 | A1 | 7/2011 | Lyyikäinen et al. |
| 2011/0226257 | A1 | 9/2011 | Lowe et al. |
| 2011/0238147 | A1 | 9/2011 | Bennett et al. |
| 2013/0255695 | A1 | 10/2013 | Jutila et al. |
| 2015/0107598 | A1 | 4/2015 | Tal et al. |
| 2016/0217707 | A1 | 7/2016 | Jutila |
| 2017/0027739 | A1 | 2/2017 | Deckman et al. |
| 2017/0196728 | A1 | 7/2017 | Lyytikainen et al. |
| 2017/0202701 | A1 | 7/2017 | Tal et al. |
| 2020/0179159 | A1 | 6/2020 | Lyytikäinen et al. |
| 2021/0298942 | A1 | 9/2021 | Jutila et al. |
| 2022/0265465 | A1 | 8/2022 | Jutila et al. |
| 2022/0265466 | A1 | 8/2022 | Jutila et al. |
| 2022/0273487 | A1 | 9/2022 | Jutila et al. |

FOREIGN PATENT DOCUMENTS

| | | | |
|---|---|---|---|
| CN | 1377635 | | 11/2002 |
| CN | 201042478 | | 4/2008 |
| CN | 201104943 | Y | 8/2008 |
| CN | 101360523 | | 2/2009 |
| CN | 201505207 | U | 6/2010 |
| DE | 8712168 | | 10/1987 |
| DE | 29819558 | | 2/1999 |
| DE | 19815552 | | 9/1999 |
| DE | 29919662 | | 3/2000 |
| EP | 0191957 | | 8/1986 |
| EP | 0798999 | | 10/1997 |
| EP | 0948948 | | 10/1999 |
| EP | 1691740 | | 8/2006 |
| ES | 0234119 | | 9/1987 |
| ES | 0295117 | | 12/1988 |
| FI | 882466 | | 11/1999 |
| FI | 0080523 | | 9/2008 |
| GB | 1039011 | | 8/1966 |
| GB | 1403393 | | 8/1975 |
| GB | 1486994 | | 9/1977 |
| GB | 1543841 | | 4/1979 |
| JP | 2010-510444 | | 4/2010 |
| NL | 8601570 | | 1/1988 |
| SU | 1377063 | | 2/1988 |
| WO | 95/28901 | | 11/1995 |
| WO | 1995028901 | A1 | 11/1995 |
| WO | 96/18365 | | 6/1996 |
| WO | 1996/18365 | | 6/1996 |
| WO | 1996/029026 | | 9/1996 |
| WO | 1999/005958 | | 2/1999 |
| WO | 00/00550 | | 1/2000 |

(56) References Cited

FOREIGN PATENT DOCUMENTS

| | | | |
|---|---|---|---|
| WO | 2001/013832 | | 3/2001 |
| WO | 03/017971 | | 3/2003 |
| WO | 2003/017971 | | 3/2003 |
| WO | 2005/048893 | | 6/2006 |
| WO | 2007/075086 | | 7/2007 |
| WO | 2010/031899 | | 3/2010 |
| WO | 2010/031900 | | 3/2010 |
| WO | 2010/031900 | A1 | 3/2010 |
| WO | 2010/031902 | | 3/2010 |
| WO | 2010/082197 | | 7/2010 |
| WO | 2010/112095 | | 10/2010 |
| WO | 2011/080164 | | 7/2011 |

OTHER PUBLICATIONS

USPTO Non-Final Office Action mailed in U.S. Appl. No. 13/771,066, May 22, 2013, 10 pages.
USPTO Final Office Action received for U.S. Appl. No. 14/088,329, Jan. 30, 2015, 18 pages.
USPTO Non-Final Office Action received for U.S. Appl. No. 14/088,329, Apr. 9, 2014, 19 pages.
USPTO Non-Final Office Action received for U.S. Appl. No. 14/088,329, Dec. 3, 2015, 19 pages.
USPTO Non-Final Office Action received in U.S. Appl. No. 13/857,134, Jul. 7, 2014, 19 pages.
USPTO Non-Final Office Action received for U.S. Appl. No. 13/119,397, Nov. 19, 2013, 19 pages.
EPO Notice of Opposition to European Patent No. EP2352470, Sep. 26, 2013, 19 pages.
USPTO Non-Final Office Action received in U.S. Appl. No. 14/590,969, Jan. 29, 2016, 20 pages.
USPTO Final Office Action received for U.S. Appl. No. 13/119,397, Jan. 12, 2016, 21 pages.
USPTO Non-Final Office Action received in U.S. Appl. No. 13/119,399, Oct. 4, 2012, 22 pages.
USPTO Non-Final Office Action received for U.S. Appl. No. 13/119,397, May 5, 2015, 23 pages.
EPO Reply to the Notice of Opposition to European Patent No. EP2352470, Apr. 25, 2014, 28 pages.
USPTO Final Office Action received for U.S. Appl. No. 13/119,397, Sep. 5, 2014, 28 pages.
PCT International Preliminary Report on Patentability mailed in PCT Application No. PCT/FI2011/050933, Apr. 30, 2013, 4 pages.
PCT International Preliminary Report on Patentability mailed in PCT Application No. PCT/FI2009/050733, Mar. 22, 2011, 6 pages.
PCT International Preliminary Report on Patentability mailed in PCT Application No. PCT/FI2009/050735, Mar. 22, 2011, 6 pages.
PCT International Search Report and Written Opinion mailed in PCT Application No. PCT/FI2011/050933, Mar. 5, 2012, 7 pages.
PCT International Search Report and Written Opinion mailed in PCT Application No. PCT/FI2009/050735, Dec. 10, 2009, 8 pages.
PCT International Search Report and Written Opinion mailed in PCT Application No. PCT/FI2009/050733, Dec. 23, 2009, 8 pages.
Johnson, et al., "Insertion and Removal of Intrauterine Devices", American Family Physician, vol. 71, No. 1, Jan. 1, 2005, pp. 95-102.
merriam-webster.com, "adhesion", Retrieved from Internet: https://www.merriam-webster.com/dictionary/adhesion, 1 pages.
USPTO, Notice of Allowance for U.S. Appl. No. 16/813,340, Apr. 22, 2022, 10 pages.
USPTO, Notice of Allowance for U.S. Appl. No. 13/882,264, Jul. 31, 2018, 10 pages.
USPTO, Notice of Allowance for U.S. Appl. No. 14/590,969, Mar. 8, 2017, 10 pages.
USPTO, Non-final Office Action for U.S. Appl. No. 13/771,066, May 22, 2013, 10 pages.
USPTO, Notice of Allowance for U.S. Appl. No. 15/647,104, Oct. 18, 2019, 10 pages.
USPTO, Non-final Office Action for U.S. Appl. No. 13/882,264, Apr. 6, 2017, 11 pages.
USPTO, Non-final Office Action for U.S. Appl. No. 13/119,401, Aug. 17, 2012, 11 pages.
USPTO, Non-final Office Action for U.S. Appl. No. 17/239,428, Jun. 21, 2023, 11 pages.
USPTO, Notice of Allowance for U.S. Appl. No. 17/743,249, Sep. 8, 2023, 11 pages.
USPTO, Notice of Allowance for U.S. Appl. No. 13/119,397, Apr. 5, 2017, 12 pages.
USPTO, Notice of Allowance for U.S. Appl. No. 17/743,236, Aug. 10, 2023, 12 pages.
USPTO, Non-final Office Action for U.S. Appl. No. 13/882,264, Nov. 28, 2017, 12 pages.
USPTO, Final Office Action for U.S. Appl. No. 13/882,264, Nov. 7, 2016, 13 pages.
USPTO, Non-final Office Action for U.S. Appl. No. 17/743,236, Feb. 10, 2023, 14 pages.
USPTO, Final Office Action for U.S. Appl. No. 14/590,969, Jul. 20, 2016, 14 pages.
USPTO, Non-final Office Action for U.S. Appl. No. 13/882,264, Mar. 24, 2016, 15 pages.
USPTO, Ex Parte Quayle Action for Design U.S. Appl. No. 29/558,312, Feb. 6, 2017, 16 pages.
USPTO, Non-final Office Action for U.S. Appl. No. 15/589,789, Dec. 30, 2019, 17 pages.
USPTO, Non-final Office Action for U.S. Appl. No. 15/589,789, May 29, 2019, 17 pages.
USPTO, Non-final Office Action for U.S. Appl. No. 17/239,417, Dec. 22, 2022, 18 pages.
USPTO, Notice of Allowance for Design U.S. Appl. No. 29/605,236, Oct. 3, 2017, 19 pages.
USPTO, Non-final Office Action for U.S. Appl. No. 17/239,417, Oct. 3, 2023, 19 pages.
USPTO, Final Office Action for U.S. Appl. No. 17/239,417, May 31, 2023, 21 pages.
USPTO, Notice of Allowance for U.S. Appl. No. 15/470,870, Nov. 8, 2017, 25 pages.
USPTO, Non-final Office Action for U.S. Appl. No. 17/743,213, Sep. 26, 2023, 26 pages.
USPTO, Final Office Action for U.S. Appl. No. 17/743,213, Jun. 14, 2023, 29 pages.
USPTO, Non-final Office Action for U.S. Appl. No. 17/743,249, Feb. 8, 2023, 30 pages.
USPTO, Non-final Office Action for U.S. Appl. No. 17/743,213, Jan. 26, 2023, 30 pages.
USPTO, Notice of Allowance for Design U.S. Appl. No. 29/558,312, Mar. 8, 2017, 5 pages.
USPTO, Non-final Office Action for U.S. Appl. No. 15/245,042, Oct. 11, 2016, 6 pages.
USPTO, Notice of Allowance for U.S. Appl. No. 16/792,748, Aug. 30, 2023, 7 pages.
USPTO, Ex Parte Quayle Action for U.S. Appl. No. 17/743,249, Jun. 27, 2023, 7 pages.
USPTO, Non-final Office Action for U.S. Appl. No. 16/792,748, May 10, 2023, 7 pages.
USPTO, Non-final Office Action for U.S. Appl. No. 16/792,748, May 20, 2022, 7 pages.
USPTO, Non-final Office Action for U.S. Appl. No. 15/470,870, May 23, 2017, 7 pages.
USPTO, Final Office Action for U.S. Appl. No. 16/792,748, Nov. 29, 2022, 7 pages.
USPTO, Notice of Allowance for U.S. Appl. No. 15/245,042, Feb. 10, 2017, 8 pages.
USPTO, Notice of Allowance for U.S. Appl. No. 15/891,187, Jun. 21, 2019, 8 pages.
USPTO, Notice of Allowance for U.S. Appl. No. 14/088,329, May 18, 2016, 8 pages.
USPTO, Final Office Action for U.S. Appl. No. 15/589,789, May 26, 2020, 8 pages.
USPTO, Non-final Office Action for Design U.S. Appl. No. 29/558,311, Oct. 24, 2017, 8 pages.

(56) References Cited

OTHER PUBLICATIONS

USPTO, Notice of Allowance for U.S. Appl. No. 15/891,187, Oct. 9, 2019, 8 pages.
USPTO, Notice of Allowance for U.S. Appl. No. 15/589,789, Dec. 31, 2020, 9 pages.
USPTO, Non-final Office Action for U.S. Appl. No. 15/891,187, Nov. 2, 2018, 9 pages.
USPTO, Non-final Office Action for U.S. Appl. No. 15/470,870, Apr. 17, 2017, 12 pages.
UPSTO, Non-final Office Action for U.S. Appl. No. 17/743,213, Sep. 26, 2023, 26 pages.
UPSTO, Final Office Action for U.S. Appl. No. 17/743,213, Jun. 14, 2023, 29 pages.
UPSTO, Non-final Office Action for U.S. Appl. No. 17/743,249, Feb. 8, 2023, 30 pages.
UPSTO, Non-final Office Action for U.S. Appl. No. 17/743,213, Jan. 26, 2023, 30 pages.
UPSTO, Notice of Allowance for U.S. Design U.S. Appl. No. 29/558,312, Mar. 8, 2017, 5 pages.
UPSTO, Non-final Office Action for U.S. Appl. No. 15/245,042, Oct. 11, 2016, 6 pages.
UPSTO, Notice of Allowance for U.S. Appl. No. 16/792,748, Aug. 30, 2023, 7 pages.
UPSTO, Ex Parte Quayle Action for U.S. Appl. No. 17/743,249, Jun. 27, 2023, 7 pages.
UPSTO, Non-final Office Action for U.S. Appl. No. 19/321,997, Dec. 18, 2025, 30 pages.

* cited by examiner

INSERTER

This application is a continuation application of U.S. patent application Ser. No. 16/792,748, filed Feb. 17, 2020 and titled "INSERTER," which is a continuation application of U.S. patent application Ser. No. 15/891,187 (now U.S. Pat. No. 10,561,524), filed Feb. 7, 2018 and titled "INSERTER," which is a continuation of U.S. patent application Ser. No. 15/470,870, filed Mar. 27, 2017 and titled "INSERTER," which is a continuation application of U.S. patent application Ser. No. 15/245,042, filed Aug. 23, 2016 and titled "INSERTER" (now U.S. Pat. No. 9,615,965), which is a continuation application of U.S. patent application Ser. No. 14/088,329, filed Nov. 22, 2013 and titled "INSERTER" (now U.S. Pat. No. 9,452,082), which is a continuation application of U.S. patent application Ser. No. 13/771,066, filed Feb. 19, 2013 and titled "INSERTER," which is a continuation application of U.S. patent application Ser. No. 13/119,401, filed Mar. 16, 2011 and titled "INSERTER," which claims priority to International Patent Application No. PCT/FI2009/050738, filed Sep. 16, 2009 and titled "AN INSERTER," which claims priority to both Finnish Patent Application No. 20085871, filed Sep. 17, 2008, and Finnish Patent Application No. 20085870, filed Sep. 17, 2008, all of which are incorporated herein by reference.

The present invention relates to an inserter for positioning an intrauterine device or an intrauterine system in the uterus as well as to a kit comprising an intrauterine system and an inserter.

BACKGROUND OF THE INVENTION

Various types of inserters have been developed for the positioning of mechanical and copper wire-containing intrauterine devices (IUDs) as well as of intrauterine systems having a drug containing cylinder (IUSs). In the following, IUD and IUS can be used interchangeably and when one is mentioned, it is to be understood that either of them can be used.

Most common inserters are constructed for introducing the device into the uterus in a contracted state. These inserters usually comprise an insertion tube having a relatively narrow diameter and a rounded, blunt end which will pass through the cervical canal easily and will not damage or injure the fundus upon contact therewith, and a plunger inside the insertion tube. Prior to insertion the device, whether an IUD or an IUS, is usually retracted into the insertion tube either by means of string(s) attached to the device and intended for the removal of the device from the uterus, or by pushing the device into the insertion tube by a plunger with inserters having a special window to adapt the device in the expanded shape (see for example GB 1 403 393). Then the insertion tube with the device therein is introduced through the cervical canal into the uterus. When the device is correctly positioned, it is released either by pushing the plunger towards the uterus or by holding the plunger steady and by retracting the insertion tube outwards. Once expulsed from the insertion tube within the uterine cavity, the device is supposed to resume its original expanded shape.

Simple rod-shaped inserters have been suggested for inserting relatively small or sufficiently flexible intrauterine devices in their original, expanded shape by using a push-in technique. With these inserters the correct positioning and a secure attachment of an IUS or IUD on the inserter as well as proper handling of the removal strings may be difficult.

The European patent application EP 1 691 740 relates to an inserter, with which the correct positioning and directional stiffness of the device in the inserter prior to and during insertion can be ensured, for instance, by shaping the forward end of the plunger such that the IUS assumes a specified constant configuration when drawn into the insertion tube. The IUS will thus not be twisted during insertion.

European patent EP 798 999 relates to an inserter, which allows the correct positioning of an IUS also in those cases in which the elongate member of a T-shaped device contains active material, which involves a diameter larger than that of an elongate member of a copper-wire IUD. The inserter comprises a plunger, a handle attached to the plunger, a string for the removal of the IUS, a cleft on the end of the handle to lock the string(s) in such a way that the IUS remains immobile in relation to the plunger, and an insertion tube around the plunger. The IUS is drawn into the insertion tube by pushing the tube over the device or by pulling on the removal threads whereafter the threads are manually locked in the cleft. The relative movement of the plunger and the protective tube is restricted by a stop member or stop members to ascertain that the correct configuration of the IUS is achieved. The stop members ensure that the front edge of the insertion tube is stopped in a configuration in which the hemispherical tips of the T-wings remain partly uncovered by the insertion tube but the wings nevertheless remain pressed against each other. This inserter overcomes many of the problems encountered with the conventional inserters, but the string(s) still need to be manually handled and locked.

Furthermore, document WO 2007/075086 shows an applicator for inserting an IUD, wherein the end of the applicator has two recesses for receiving the flexible arms of the IUD, and for fixing them during insertion. Document NL 8601570 shows an IUD comprising a rod which one end is secured to a ring of resilient material. The IUD, when inserted, is positioned on an insertion tube such that the rod is inside the tube and the ring outside of it.

The inserters described in these documents overcome many of the problems encountered with the conventional inserters, but the string(s) still need to be handled and manually locked. Further, the inserters are designed primarily for the insertion of the conventional devices which are to be inserted in a compressed configuration. Therefore there is still need for an improved kit comprising an intrauterine system and an inserter.

OBJECT AND SUMMARY OF THE INVENTION

An object of the invention is to provide a simple, easy to use inserter and kit comprising an intrauterine system and an inserter for the positioning of an intrauterine system in the uterus by solving at least partially at least some of the problems mentioned above. An object of the invention is particularly to provide an inserter and a kit with which, during the insertion process, no manual handling of the strings as such is needed. A further object of the invention is to provide an inserter having an improved system for locking and releasing the removal strings of an IUS in the necessary steps during the insertion process. A typical inserter for an intrauterine system according to the present invention comprises a handle and an insertion tube having a first end and a second end, and being arranged in connection with the handle. The inserter is characterized in that the first end of the insertion tube comprises at least one frame slot for receiving a frame of the intrauterine system.

A typical kit comprising an inserter and an intrauterine system, according to the present invention, is such that the inserter is according to the present invention, the intrauterine system comprises a therapeutic component and a continuous, closed frame, the therapeutic component being connected to the frame at at least one point, and the therapeutic component of the intrauterine system is at least mainly arranged inside the first end of the insertion tube and the frame of the intrauterine system is at least mainly arranged outside the first end of the insertion tube.

DETAILED DESCRIPTION OF THE INVENTION

Figure 1:
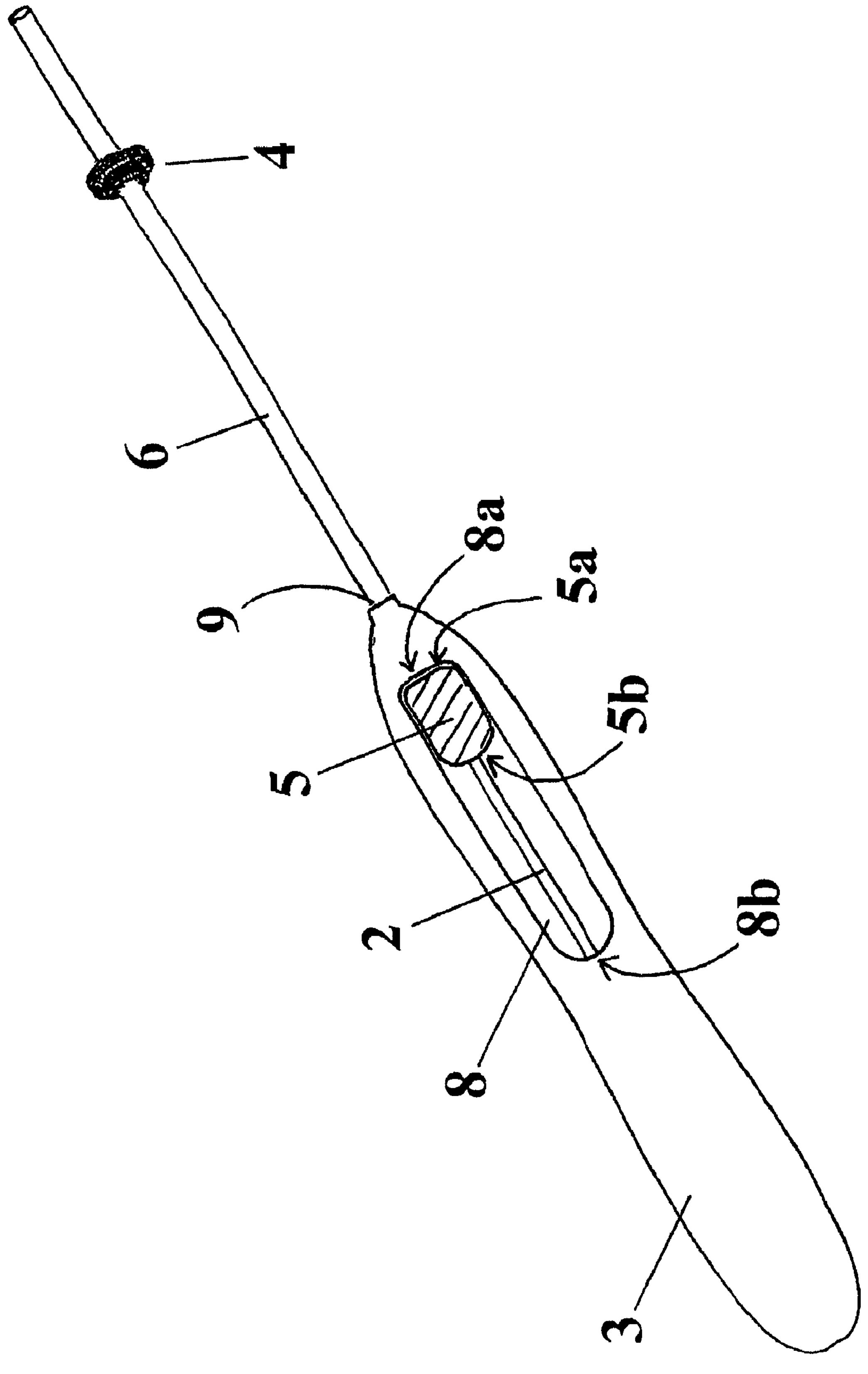
FIG. 1 illustrates a general overview of an inserter that is part of a kit according to an embodiment of the invention.

A typical inserter for an intrauterine system according to the present invention comprises a handle and an insertion tube having a first end and a second end, and being arranged in connection with the handle. The inserter is characterized in that the first end of the insertion tube comprises at least one frame slot for receiving a frame of the intrauterine system.

The invention therefore provides an easy to use inserter and kit comprising the device and the inserter, by which only few simple steps are needed to prepare for the insertion and to securely install and position an intrauterine system into the uterus.

In the present description and claims, the therapeutic component is a component capable of inducing a therapeutic effect, for example by releasing an active agent such as copper ions or hormones. Moreover, by first ends are typically meant the ends that are closer to the uterus during the insertion of the intrauterine system. Second ends are the ends opposite to the first ends. Moreover, the terms IUS or IUD and removal strings are used when describing the preferred embodiment of the present invention, but these are not to be construed as limiting the claims.

There are at least two different ways of arranging the insertion tube in connection with the handle. Indeed, according to an embodiment of the invention, the inserter is further characterised in that the handle has a longitudinal opening at its first end, said opening having a longitudinal axis parallel to the longitudinal axis of the inserter, a first end and a second end, and the inserter further comprises a movable slider arranged in said longitudinal opening and having a first end and a second end, a plunger attached to the handle, the second end of the insertion tube being attached to the slider.

According to another embodiment, the second end of the insertion tube is directly attached to the handle.

The longitudinal opening on the handle can also be quite narrow and does not need to be symmetrically positioned on the handle and with respect to the longitudinal axis.

A typical kit comprising an inserter and an intrauterine system, according to the present invention, is such that the inserter is according to the present invention, the intrauterine system comprises a therapeutic component and a continuous, closed frame, the therapeutic component being connected to the frame at at least one point, and the therapeutic component of the intrauterine system is at least mainly arranged inside the first end of the insertion tube and the frame of the intrauterine system is at least mainly arranged outside the first end of the insertion tube.

In the following, several different embodiments of the present invention, both the inserter and the kit, are discussed. The information given applies mutatis mutandis to both the inserter and the kit.

According to another embodiment of the invention the therapeutic component is selected from the group consisting of a reservoir for active agent, a metallic wire and a combination thereof. For example, the reservoir may essentially consist of an elastomer and an active agent, or the metal wire can be made of copper.

According to an embodiment of the invention, the reservoir of the intrauterine system essentially consists of an elastomer and an active agent. The reservoir can be for example as described in WO 2003/017971, U.S. Pat. Nos. 6,056,976, 6,299,027 or WO 00/00550, the contents of which are hereby incorporated by reference.

The elastomer can be for example an elastomer composition comprising a siloxane based elastomer, a thermoplastic polyurethane, a thermoplastic polyurethane elastomer, ethyl vinyl acetate, a polyolefin-based elastomer, a silicone containing thermoplastic polyurethane or a mixture of at least two of these. The reservoir may also be of a core and membrane-type, wherein both parts are preferably made of an elastomer composition.

The intrauterine system also preferably comprises strings for removal, location or detection of the system, as well as at least one image enhancing means for improving the detection and/or location of the system.

The image enhancing means can be for example selected from the group consisting of a) an inert metal coating on at least part of the body of the intrauterine system;

b) inert metal inserts, clips, rings or sleeves fixedly positioned on the body of the intrauterine system;

c) metal or ferromagnetic powder or particles or suitable metal or alkali metal salts mixed during the compounding step in the raw materials of the frame, core matrix or membrane of the intrauterine system, and d) a metallic cup, connector, adapter, clamp, sleeve or holder fixed at a suitable position on the frame, which can also be used to anchor or join the therapeutic component onto the frame.

According to another embodiment of the invention, the therapeutic component is connected to the frame in at least one point. Moreover, the intrauterine system can be connected to the inserter for example via at least one connection part. The connection part is preferably designed such that it enhances the retention of the device on the inserter prior and during the insertion of the device.

The connection part can be for example a hollow knob, adapted to receive a pin, one of these parts being arranged on the intrauterine system and the other on the inserter. Another option is to use a traditional ball joint. A person skilled in the art is readily able to find a suitable solution for this connection part.

Also in view of this, and according to an embodiment of the invention, the first end of the insertion tube comprises at least one connection slot for receiving the connection part of the intrauterine system. Alternatively, the first end of the plunger may comprise a slot for receiving the intrauterine system, for example for receiving the second end of the frame or of the therapeutic component of the intrauterine system. The first end of the insertion tube may also comprise two diagonally symmetrical connection slots for receiving the connection part of the intrauterine system. It is naturally possible that there are more than two connection slots, such as three, four, five or six slots. The connection part then preferably comprises suitable parts fitting to these connections slots. The connection part can also be made to fit on the plunger. If a plunger is used, it can be designed to receive the therapeutic component or the frame.

According to the invention, the first end of the insertion tube comprises at least one frame slot for receiving the frame of the intrauterine system. The first end of the insertion tube may also comprise two diagonally symmetrical frame slots for receiving the frame of the intrauterine system. The number of frame slots can also be higher, such as three, four, five or six. The frame slots can be parallel to the longitudinal axis of the insertion tube or non-parallel to it. The frame slots can for example be straight or slightly curved with respect to the outer surface of the insertion tube, in order for allowing the frame to be released. The frame slots are preferably narrow enough to prevent the therapeutic component from slipping out and long enough to allow the movement of the therapeutic component and the stretching/compression of the frame during the insertion step. The insertion tube is large enough for containing the therapeutic component. The frame slot(s) together with connection parts assure that the intrauterine system will be securely fitted and in the correct configuration during the insertion.

According to an embodiment of the invention, the shape of the frame of the device is selected from the group consisting of annular, circular, oval, spiral, toroidal, triangular, polygonal, almond-shape, shield-shape and diamond-shape. The frame is also preferably made of an elastic material, such as an elastomer composition as mentioned above in connection with the reservoir. The frame may include, for example as a core material, thin metallic wire made for example from a metallic memory material or other suitable material that is elastic enough for allowing the insertion, i.e. collapsing during the insertion through the cervical canal but returning to its original shape once in place in the uterus.

According to one embodiment of the invention, when the present inserter is in use, the therapeutic component of the intrauterine system is preferably at least mainly arranged inside the insertion tube and the frame of the intrauterine system is preferably at least mainly arranged outside the insertion tube.

According to another embodiment of the invention, the inserter further comprises a flange arranged on the insertion tube. This flange can be adjusted to correspond to the depth of the uterus in order to correctly position the device during its insertion.

According to one embodiment of the invention, the first end of the opening and the first end of the slider form a first pair of stop members, and the second end of the opening and the second end of the slider form a second pair of stop members.

A part of the handle can thus comprise an opening having a first end and a second end and running in the longitudinal direction of the plunger. The opening can have at the first end a channel in which the insertion tube can slide in the longitudinal direction. At the second end, i.e. distal end (away from the uterus) the insertion tube is attached to the slider or to a means which can be used to move the slider and preferably forms at least a part of the slider. With respect to the starting configuration, the front surface of said means and the surface at the first end of the opening, the end directed towards the IUS, together form the first pair of stop members. To release the IUS after it has been positioned in the uterus the slider and the insertion tube will be pulled backwards past the plunger the distance determined by the second pair of stop members, formed by the rear surface of the means to move the slider and the surface at the second end of the opening.

The handle can have many shapes and is designed for easy handling of the inserter even by using only one hand. The plunger attached to the handle is advantageously hollow or has a groove or bore running in the axial direction thus allowing the string(s) to slide freely in it, without any risk of them getting jammed between the plunger and the insertion tube. The first end, i.e. the forward end of the plunger is preferably suitably shaped to have for example a notch, an indentation, an eyelet, a funnel or a groove to adapt the lower end of the device and to enable the optimal and secure positioning of the device on the plunger.

The forward parts (parts directed towards the uterus) of the plunger and the insertion tube can be straight or curved so as to conform to the anatomy of the uterus. Preferably these parts are made from a flexible material in order to avoid perforation of the uterus.

The slider mechanism is preferably inside the handle and comprises at least one elongated element, which can be moved in the longitudinal direction of the plunger. According to an embodiment of the invention the slider comprises a means to move the slider, which preferably is a part of the slider, and the insertion tube attached to said means. According to another embodiment of the invention the slider comprises at least two elements, preferably parallel, which are combined on at least one point by a transversal member. The transversal member may form means, for example a knob or switch, by which the slider can be moved. The handle can comprise one or more means to connect the slider elements and to facilitate the movement of the slider, for example a support, a shoulder, a holder, a saddle, a groove or a slot. The slider preferably comprises at least one structural element, for example an extension, which is capable to generate the necessary operation of a locking means to keep the strings immobilized during storage or during preparatory steps before insertion and/or to release the string(s) when the slider is moved to the backward position.

The inserter according to the present invention may thus also comprise locking means for reversibly locking the intrauterine system in relation to the plunger, said locking means being controllable by the slider and/or the insertion tube. This means that the locking means can also be controlled by a part of the slider and/or of the insertion tube, such as an extension of either or both of them. The reversible locking of the intrauterine system can be for example achieved by locking the removal string or strings of the intrauterine system, in such a way that the device remains immobile in relation to the plunger during the necessary steps prior to and during insertion but can be released after the IUS has correctly been positioned in the uterus. Therefore no manual handling of the strings as such is needed, which increases security and hygiene.

The locking means is any arrangement which, induced by the movement of the slider or of the means to move the slider and the insertion tube, can immobilise the removal string(s) to hold the IUS in a stable position and/or to release the string(s) after insertion to release the IUS. Particularly, the invention relates to a locking means which comprises an object capable of reversibly preventing or allowing the movement of the string(s) by at least partly moving or pivoting from the original position, for example rotating around a shaft or an axle, and vertically or horizontally attached to the handle. The object may have several shapes and may be for example round or rod-shaped, wedge, polygonal or rectangular with rounded or sharp corners. The surface of the object preferably comprises one or more extensions having variable size and shape, for example a knob, a rib or a switch. When the slider mechanism is moving backwards, at a suitable point a part or an extension of the slider or of the insertion tube is pressed against at least one extension of the object thus changing its orientation enough relative to the original position to cause release of the string(s). Preferably the object has a slot or pinhole through which the string(s) run.

The locking means may also comprise at least one counterpart against which the string(s) are pressed by the object and thus reversibly immobilized in the locking position. The counterpart has a suitable shape adapted to fit at least some part of the surface of the object. An extension, or extensions of the object can be used to keep the object and the counterpart in a fixed configuration until the slider is moved backwards to release the IUS. The counterpart preferably has a suitable design to keep the string(s) in proper direction, for example a slot or pinhole through which the string(s) run. Further, the object and said at least one counterpart have preferably a suitable length and diameter to fit inside the handle.

According to one embodiment of the invention, the locking means thus comprises

- a main part,
- a first extension of the main part having an abutment surface,
- a counterpart adapted to form a blocking together with the main part, wherein the locking means is rotatably mounted on the inserter.

According to another embodiment of the invention the main part comprises an opening or a slot in a diagonal direction through essentially the whole diameter of the main part, adapted to receive at least one removal string of the intrauterine system.

The locking means can be for example mounted on the handle of the inserter. According to another embodiment of the invention the opening or slot of the main part is adapted to receive a removal string of the intrauterine system.

According to yet another embodiment of the invention, the locking means comprises a main part,

- a first extension of the main part having an abutment surface,
- a second extension of the main part having a wedge-like shape,
- a counterpart, wherein the second extension is adapted to form a blocking together with the counterpart and the locking means is rotatably mounted on the inserter.

According to one embodiment of the invention, the main part has essentially the shape of a cylinder, or it is of triangular shape, or of any other suitable shape.

According to one embodiment of the invention the slider comprises an extension adapted to abut on the abutment surface of the first extension of the main part of the locking means.

According to one other embodiment of the invention the locking means comprises a main part comprising a first extension and a second extension arranged, in their initial position, to be essentially in contact with each other to from a blocking, wherein the slider, a part of the slider, the insertion tube or a part of the insertion tube is arranged to protrude into the main part of the locking means so as to separate the first and second extensions from each other.

According to yet one other embodiment of the invention the locking means comprises

- a first locking part and a second locking part movably mounted on the inserter and arranged, in their initial position, to be essentially in contact with each other to form a blocking, and
- a first protrusion and a second protrusion arranged on a location selected from the group consisting of the inner surface of the insertion tube, the outer surface of the insertion tube, the inner surface of the slider and the outer surface of the slider, wherein the first and second protrusions are arranged to move the first and second locking parts when moving the slider or the insertion tube.

The locking means could also be welding, gluing, cutting, knot or adhesion. The strings could thus be for example attached to the body of the inserter by welding (for example by heating), gluing with glue or attaching with an adhesive agent (such as sticker). The slider or the insertion tube would then release the attachment when moving to release the device. Other options could be a knot or other mechanical hindrance, when the slot provided for the strings is larger in the releasing position. The slider could also comprise a blade that cuts the strings loose from the inserter.

It is obvious to a person skilled in the art that, in accordance with the above description, the locking means can be of any other kind than those specifically listed above as well as a combination thereof.

During the preparatory steps the string(s) are locked but they are released automatically by the slider, when it is drawn backwards in order to release the IUS. As compared to previous inserters there is no need to manually handle the removal strings during the preparatory steps and during insertion, which eliminates the possibility of user-made mistakes.

The present invention also relates to a use of the kit according to the invention. Any details and embodiments listed above naturally apply mutatis mutandis to the use according to the invention.

The present invention also relates to a method for positioning an intrauterine system in a uterus of a patient, wherein the method uses a kit according to the present invention.

The method comprises the steps of sounding the uterus using a probe, for determining the correct insertion depth, introducing the inserter into the uterus of the patient until the intrauterine system is in its correct location, removing the inserter from the uterus of the patient.

The method advantageously contains, as a second step, setting the flange to show the correct insertion depth. Depending on the inserter, the method may also comprise, after the introduction of the inserter into the uterus, the step of moving the slider towards the second end of the opening until the second end of the opening is in contact with the second end of the slider, thus releasing the intrauterine system from the inserter.

An example of the method for positioning the intrauterine system is given hereafter. To insert the IUS only few steps are needed. To prepare for the insertion the sterile package is carefully opened. The IUS is positioned at the forward end of the plunger or of the insertion tube in the expanded configuration. The removal string(s) attached to the device are preferably immobilised by the locking means to keep the IUS at a steady and correct position until it is released in the uterus.

The inserter is introduced into the uterus until the IUS is in the correct location, which is determined beforehand by using a probe and preferably shown by the flange set at the correct insertion depth. Depending on the inserter, the slider is then moved towards the second end of the opening until the second end of the opening is in contact with the second end of the slider, thus releasing the intrauterine system from the inserter. The inserter is then removed and the IUS remains in place. The inserter thus allows easy and secure positioning of an IUS.

DETAILED DESCRIPTION OF THE DRAWING

In the following description, the term slider and the corresponding reference number are used to designate both the slider itself and the means to move the slider attached to the slider. The term slider is used for convenience of reading.

FIG. 1 illustrates a general overview of an inserter according to the invention. The inserter comprises a handle 3, a plunger 2 attached to the handle, a slider 5, an insertion tube 6 around the plunger, the second end of the insertion tube being attached to the slider or to the means to move the slider. The inserter also comprises means for reversibly locking the string(s) (not shown) in such a way that the IUS remains immobile in relation to the plunger during the necessary steps prior to and during insertion, and again for releasing the string(s) and the IUS after it has been inserted. The inserter further comprises an opening 8 in a part of the handle, a channel 9 in which the insertion tube slides in the longitudinal direction, and a flange 4, which can be adjusted so that its distance from the front end of the intrauterine system corresponds to the depth of the uterus.

The part of the handle 3 that is closer to its first end has an opening 8 having a first end 8*a* and a second end 8*b*, which opening runs in the direction of the plunger 2 and has at its first end a channel 9 in which the insertion tube 6 slides in the longitudinal direction. In the original configuration the first end 5*a* of the slider 5 abuts the first end 8*a* of the opening 8 of the handle 3. The surface of the second end 5*b* of the slider 5 and the surface at the second end 8*b* of the opening 8 together form a pair of stop members. At the second end of the handle, i.e. at the end farther away from the uterus, the insertion tube is attached to the slider 5. After the IUS has been inserted, the slider and the insertion tube can be moved backwards until the surfaces 5*b* and 8*b* contact each other. The locking means are arranged inside the handle 3 and are thus not visible.

Figures 2A, 2B:
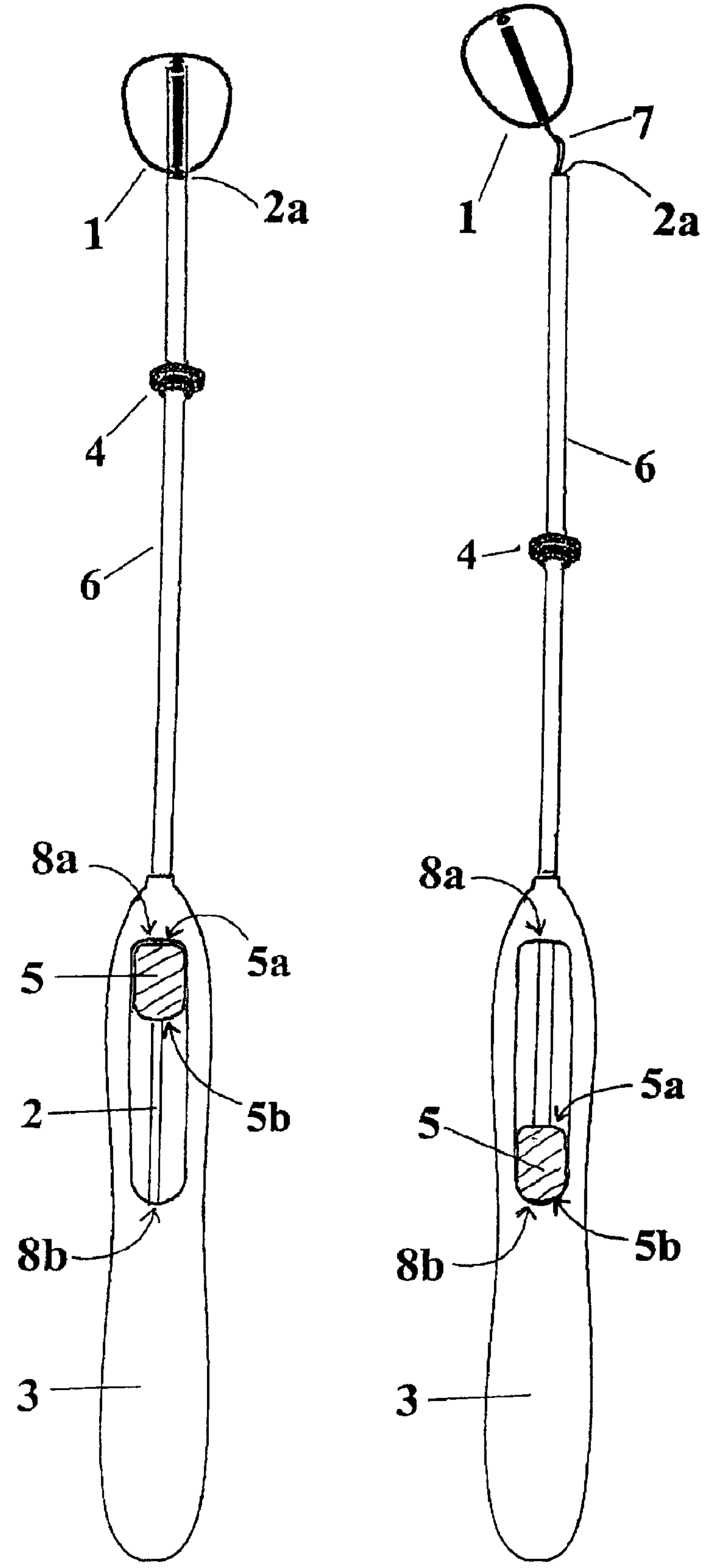
FIGS. 2A and 2B illustrate an operating principle of an inserter that is part of a kit according to an embodiment of the invention.

FIGS. 2A and 2B illustrate an operating principle of an inserter according to an embodiment of the invention.

FIG. 2A shows an inserter and an almond-shaped IUS 1 in a configuration as they are in a sterilized package. The IUS is placed in the first end (i.e. the front end, i.e. the entry into the uterus) of the inserter so that the drug containing reservoir of the device is inside the insertion tube 6 with the bottom tip of the frame, the reservoir or the loop abutting the end of the plunger (shown with reference number 2*a*). The means to move the slider 5 is on the basic position, and the removal string(s) (7, shown in the FIG. 2B) inside the inserter are tightened and locked by the locking means.

FIG. 2B illustrates the procedure to release the IUS. The device in the configuration according to FIG. 2A is introduced into the uterus until the IUS is in the correct location, where after the device is released from the insertion tube. While retaining the inserter stationary, the insertion tube is retracted towards the handle by moving the slider 5 backwards until the surface 5*b* of the slider abuts the surface 8*b* of the opening 8. The distance the slider and the insertion tube can be moved has been selected to indicate clearly the moment at which the IUS has completely been released from the insertion tube moving towards the handle.

Figure 3A:
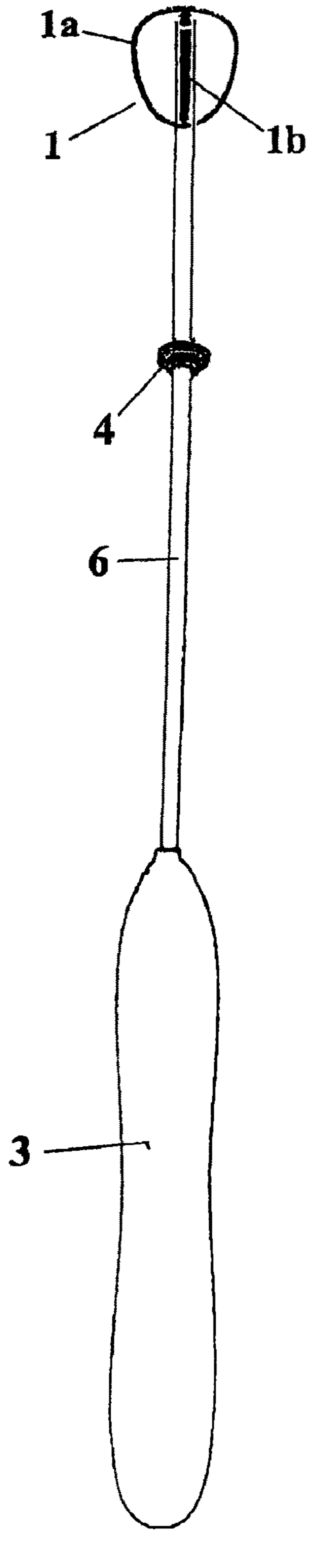
FIGS. 3A and 3B illustrate a an operating principle of an inserter that is part of a kit according to another embodiment of the invention.
Figure 3B:
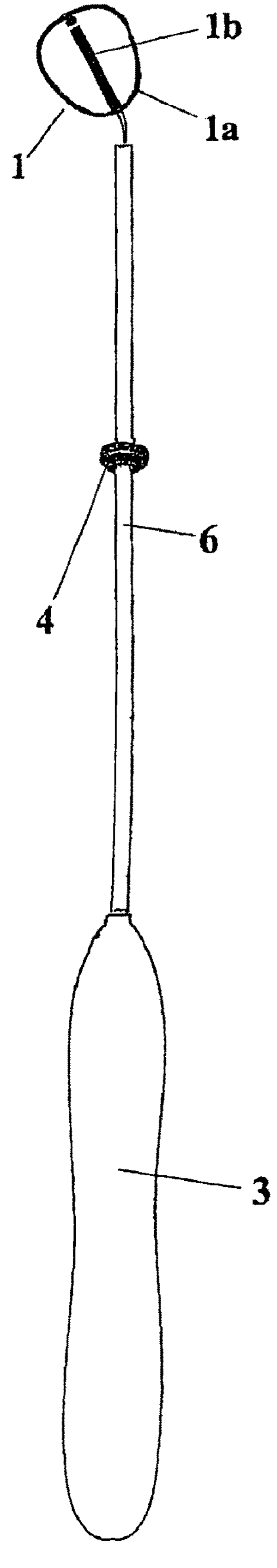

FIGS. 3A and 3B illustrate another embodiment of the invention, an operating principle of an inserter which does not have a plunger or a slider. The frame of the IUS is marked with the reference number 1*a*, and the therapeutic component with reference number 1*b*.

Figure 4A:
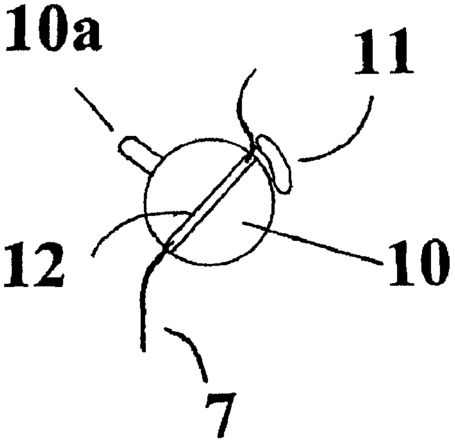
FIGS. 4A and 4B illustrate a locking means usable in an embodiment of the invention.
Figure 4B:
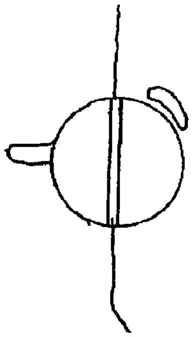

FIGS. 4A and 4B illustrate a locking means according to an embodiment of the invention. The locking means are arranged preferably at the inside of the handle 3, on any of the inside surfaces of the handle. The locking means are used to immobilise and release the string(s) of the IUS.

FIG. 4A illustrates a locking means according to an embodiment of the invention comprising a main part 10 having essentially the shape of a cylinder and comprising an opening 12 there through in a diagonal direction. The string(s) 7 of the IUS pass through the opening 12. The main part 10 is rotatably mounted on the handle, on a shaft or an axle (not shown). The locking means also comprises a counterpart 11, such that in the locking position the string(s) are immobilized between the counterpart and the main part. The counterpart thus has a suitable shape adapted to fit to a part of the surface of the main part. When the slider is moving backwards, at a suitable point a part or an extension of the slider is pressed against the extension 10*a* of the main part 10 thus turning it enough to release the string(s), as shown in FIG. 4B.

Figure 5A:
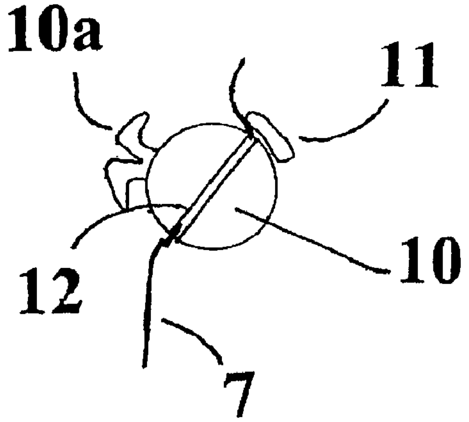
FIGS. 5A and 5B illustrate a locking means usable in another embodiment of the invention.
Figure 5B:
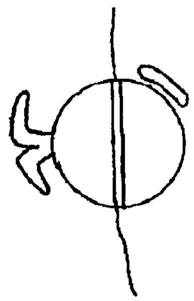

FIGS. 5A and 5B illustrate a locking means according to another embodiment of the invention. FIG. 5A illustrates an object similar to the one presented in FIG. 4A, but having a different construction of the extension 10*a*.

Figure 6A:
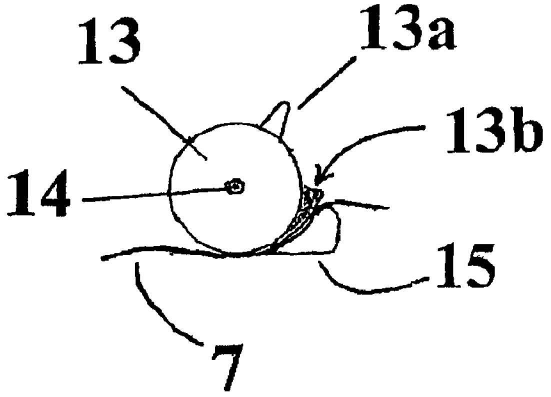
FIGS. 6A and 6B illustrate a locking means usable in yet another embodiment of the invention.
Figure 6B:
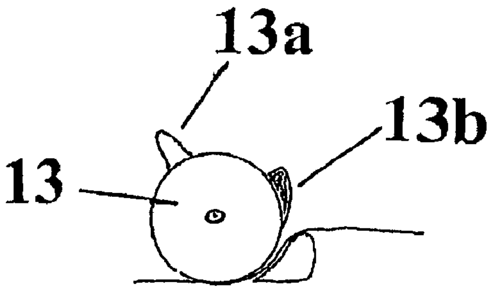

FIGS. 6A and 6B illustrate a locking means according to yet another embodiment of the invention. This is a side view of a cylindrically shaped locking means, having a main part 13 which comprises two extensions 13*a* and 13*b*. The locking means can rotate around a shaft or an axle 14 and is preferably attached to a shorter side of the inner surface of the handle. The locking means also comprises a counterpart 15 such that the string(s) 7 are immobilised between the counterpart 15 and the extension 13*b*. The counterpart 15 has a suitable shape adapted to fit to a part of the surface of the extension 13*b*. When the slider is moving backwards, at a suitable point a part or an extension of the slider is pressed against the extension 13*a* thus turning it enough to release the string(s), as shown in FIG. 6B. In this case the handle can also comprise a groove in which the string(s) run (not shown).

Figure 7A:
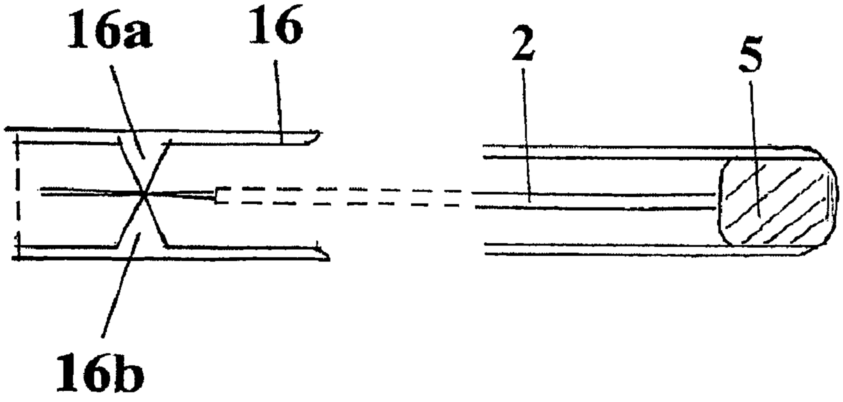
FIGS. 7A and 7B illustrate a locking means usable in still a further embodiment of the invention.
Figure 7B:
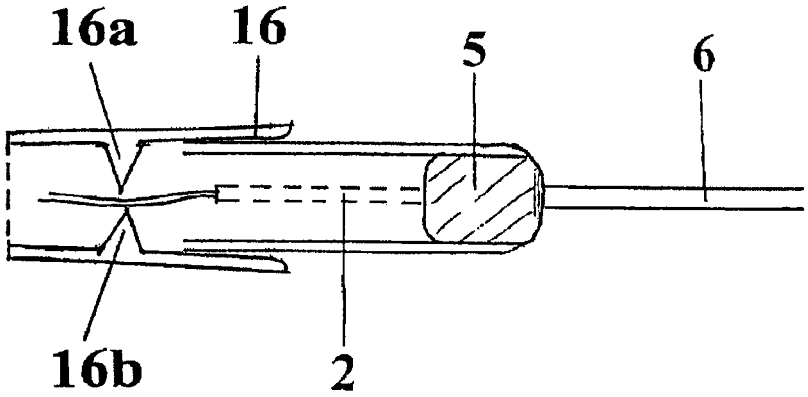

FIGS. 7A and 7B illustrate a locking means according to an embodiment of the invention. The locking means 16 comprises two extensions 16*a* and 16*b* to immobilize the strings as shown in FIG. 7A. When the slider 5 and the insertion tube 6 move backwards the slider and/or the insertion tube protrudes into the locking means at least partly to expand the means enough to separate the extensions and to release the strings, as shown in FIG. 7B.

Figure 8A:
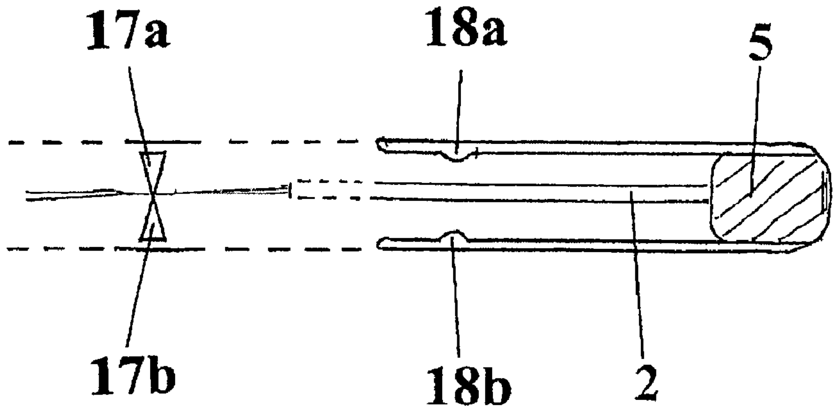
FIGS. 8A and 8B illustrate a locking means usable in a further embodiment of the invention.
Figure 8B:
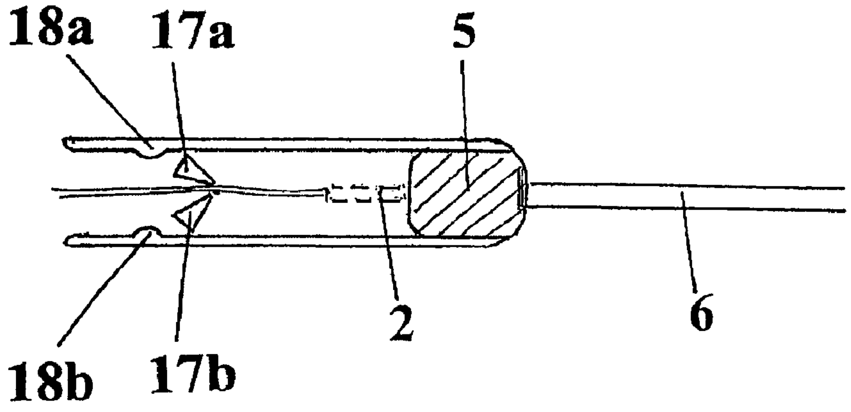

FIGS. 8A and 8B illustrate a locking means according to a further embodiment of the invention. The locking means comprises two parts 17*a* and 17*b* to immobilize the strings as shown in FIG. 8A, said parts being able to move or turn from the original position. The slider 5 has two extensions 18*a* and 18*b*. When the slider 5 and the insertion tube 6 move backwards the slider extensions turn the locking parts 17*a* and 17*b* apart from each other enough to release the strings, as shown in FIG. 8B.

Figure 9A:
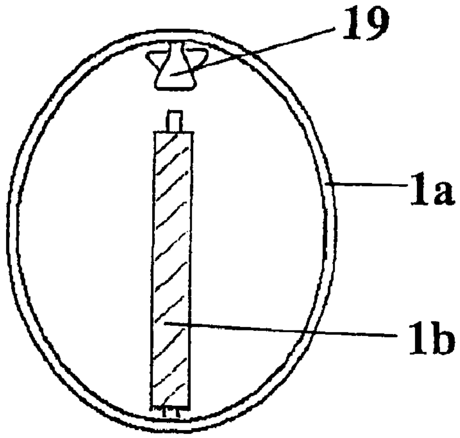
FIGS. 9A, 9B, 9C and 9D illustrate intrauterine systems and their positioning on an inserter according to some embodiments of the invention.
Figure 9B:
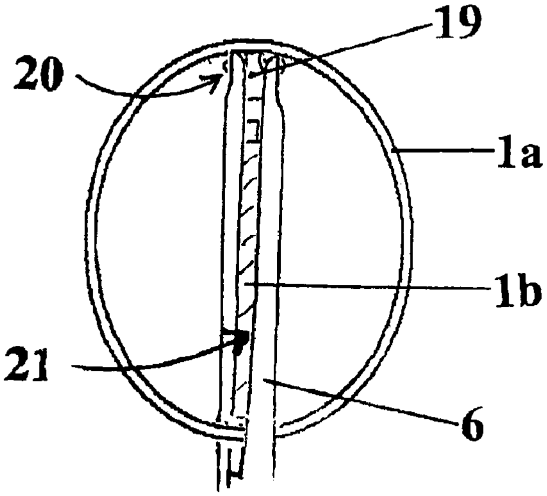

FIGS. 9A and 9B illustrate an intrauterine system and its positioning on the inserter according to an embodiment of the invention. The intrauterine system has a frame 1*a* and a therapeutic component 1*b* and it is positioned in the insertion tube 6. The intrauterine system is connected to the inserter via one connection part 19. The first end of the insertion tube 6 comprises one connection slot 20 for receiving the connection part 19. The therapeutic component is essentially completely and the frame essentially only partly positioned in a frame slot 21.

Figure 9C:
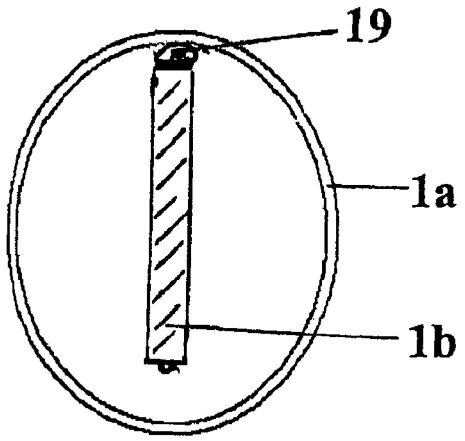
Figure 9D:
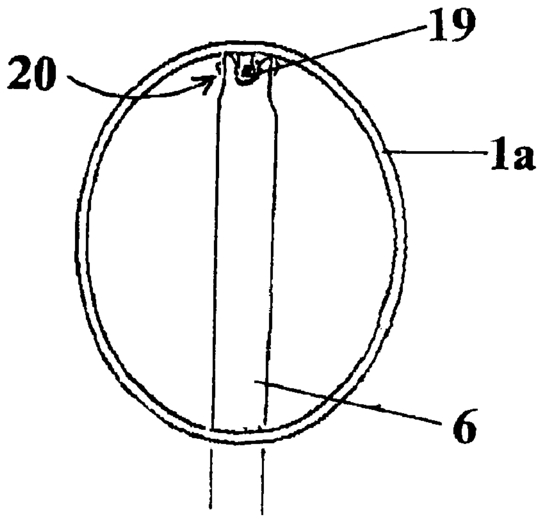

FIGS. 9C and 9D illustrate another intrauterine system and its positioning on the inserter according to another embodiment of the invention. The intrauterine system has the same parts as in FIGS. 9A and 9B. The therapeutic component is essentially completely positioned inside the insertion tube and the frame is essentially completely outside the insertion tube.

Figure 10A:
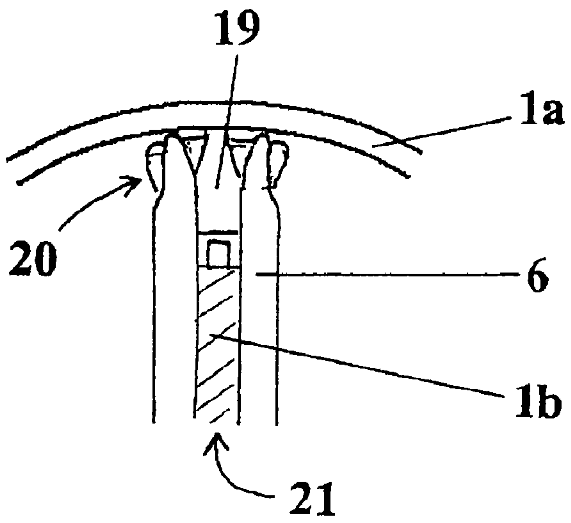
FIGS. 10A and 10B illustrate some details of FIG. 9B.
Figure 10B:
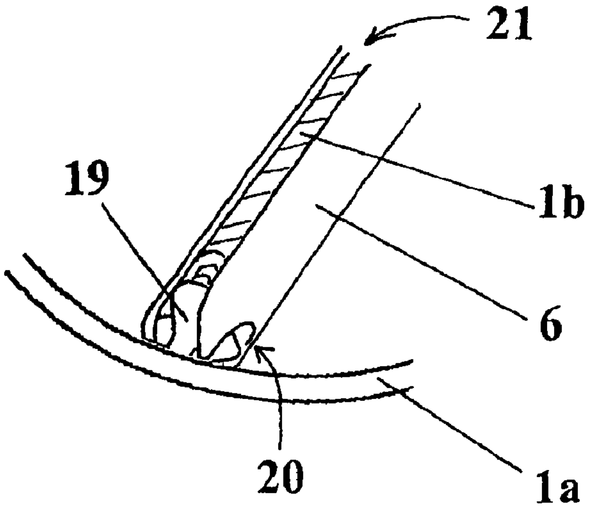

FIGS. 10A and 10B illustrate some details of FIG. 9B, namely the first end of the insertion tube 6 and the connection of the intrauterine system on the insertion tube.

The invention claimed is:

1. A kit comprising:
an intrauterine system comprising:
a reservoir containing a hormone; and
a removal string attached to the intrauterine system; and
an inserter comprising:
a handle comprising a movable slider arranged in a longitudinal opening;
a plunger attached to the handle;
an insertion tube attached to the slider; and
a lock arranged inside the handle, the locking means lock being controllable by the slider,
wherein the lock comprises:
a first locking part and a second locking part movably mounted inside the handle and arranged in a first position of the slider to be essentially in contact with each other to form a blocking and lock the intrauterine system in relation to the plunger via the removal string; and
a first protrusion and a second protrusion arranged inside the handle,
wherein the first and second protrusions are arranged to move the first and second locking parts in response to movement of the slider to a second position and release the removal string and intrauterine system.

2. The kit of claim 1, wherein the inserter further comprises an adjustable flange arranged on the insertion tube.

3. The kit of claim 2, wherein the hormone is levonorgestrel.

4. The kit of claim 1, wherein the removal string is contained wholly within the insertion tube and the handle.

5. The kit of claim 4, wherein the hormone is levonorgestrel.

6. The kit of claim 1, wherein the intrauterine system further comprises image enhancing means.

7. The kit of claim 6, wherein the hormone is levonorgestrel.

8. The kit of claim 1, wherein the hormone is levonorgestrel.

9. A method of preventing pregnancy or providing contraception in a patient, comprising:
(a) providing an intrauterine system having a reservoir containing a hormone and a removal string attached to the intrauterine system;
(b) holding an inserter in one hand, the inserter comprising:
a handle comprising a movable slider arranged in a longitudinal opening;
a plunger attached to the handle;
an insertion tube attached to the slider; and
a lock arranged inside the handle, the lock being controllable by the slider,
wherein the lock comprises:
a first locking part and a second locking part movably mounted inside the handle and arranged in a first position of the slider to be essentially in contact with each other to form a blocking and lock the intrauterine system in relation to the plunger via the removal string; and
a first protrusion and a second protrusion arranged inside the handle,
wherein the first and second protrusions are arranged to move the first and second locking parts in response to movement of the slider to a second position and release the removal string and intrauterine system;
(c) introducing the inserter into a uterus of the patient with the one hand; and
(d) moving the slider with one digit of the one hand, thereby releasing the removal string and intrauterine system within the uterus.

10. The method of claim 9, where the inserter further comprises an adjustable flange arranged on the insertion tube.

11. The method of claim 10, further comprising:
sounding the uterus to predetermine a depth for placement of the intrauterine system; and
adjusting the flange to correspond to the predetermined depth.

12. The method of claim 11, wherein the hormone is levonorgestrel.

13. The method of claim 10, wherein the hormone is levonorgestrel.

14. The method of claim 9, wherein the removal string is contained wholly within the insertion tube and the handle.

15. The method of claim 14, wherein the hormone is levonorgestrel.

16. The method of claim 9, wherein the intrauterine system further comprises image enhancing means.

17. The method of claim 16, wherein the hormone is levonorgestrel.

18. The method of claim 9, wherein the hormone is levonorgestrel.

* * * * *